United States Patent
Lieberman

(10) Patent No.: US 7,160,561 B2
(45) Date of Patent: Jan. 9, 2007

(54) HERBAL COMPOSITION AND METHOD OF TREATING HIV INFECTION

(75) Inventor: Chaim Jeremiah Lieberman, Brooklyn, NY (US)

(73) Assignee: Amazon Biotech Inc., New York, NY (US)

( * ) Notice: Subject to any disclaimer, the term of this patent is extended or adjusted under 35 U.S.C. 154(b) by 0 days.

(21) Appl. No.: 10/848,463

(22) Filed: May 18, 2004

(65) Prior Publication Data

US 2004/0265335 A1 Dec. 30, 2004

Related U.S. Application Data

(60) Provisional application No. 60/471,928, filed on May 19, 2003.

(51) Int. Cl.
*A61K 36/324* (2006.01)
*A61K 36/54* (2006.01)
*A61K 36/8962* (2006.01)

(52) U.S. Cl. ............... 424/739; 424/725; 424/754; 424/756; 424/773; 424/775; 424/777; 424/779

(58) Field of Classification Search ......... 424/725, 424/739, 754, 756, 773, 775, 777, 779
See application file for complete search history.

(56) References Cited

U.S. PATENT DOCUMENTS

| | | |
|---|---|---|
| 5,108,750 A | 4/1992 | Liu |
| 5,707,631 A | 1/1998 | Lieberman |
| 5,858,370 A | 1/1999 | Deans et al. |
| 5,989,556 A | 11/1999 | Tsai |
| 6,214,350 B1 | 4/2001 | Hwang |
| 6,280,751 B1 | 8/2001 | Fletcher |
| 6,541,045 B1 | 4/2003 | Charters et al. |
| 6,629,835 B1 | 10/2003 | Babish |
| 6,696,094 B1 | 2/2004 | Wu |
| 2003/0003167 A1 | 1/2003 | Jung et al. |
| 2003/0026859 A1 | 2/2003 | Goren et al. |
| 2003/0185907 A1 | 10/2003 | Krumhar |
| 2004/0009240 A1 | 1/2004 | Solanki |
| 2004/0009245 A1 | 1/2004 | Vail, III |
| 2004/0023894 A1 | 2/2004 | Hasier-Nguyen |
| 2004/0028751 A1 | 2/2004 | Mae et al. |
| 2004/0109904 A1 | 6/2004 | Li |
| 2004/0116394 A1 | 6/2004 | Mukherjee et al. |
| 2004/0146588 A1 | 7/2004 | Kogan |
| 2004/0151792 A1 | 8/2004 | Tripp |
| 2004/0156920 A1 | 8/2004 | Kane |

FOREIGN PATENT DOCUMENTS

| | | |
|---|---|---|
| GB | 2 388 539 | 11/2003 |
| WO | WO 94/18993 | 9/1994 |
| WO | WO 99/51249 | 10/1999 |
| WO | WO 03/006036 A2 | 1/2003 |

*Primary Examiner*—Susan Coe Hoffman
(74) *Attorney, Agent, or Firm*—Cohen, Pontani, Lieberman & Pavane

(57) ABSTRACT

A therapeutic herbal composition is beneficial for enhancing the immune system and treating such a diverse range of diseases as cancer, AIDS, Epstein Barr syndrome and depression. It is also useful as a general blood tonic. This composition includes the synergistic combination of *Boswelia carterii* stem resin, *Styrax benzoin* stem resin, *Cinnamomum zeylanicum* bark, *Curcuma zedoaria* root, *Syzygium aromaticum* fruit, *Nardostachys chinensis* root, *Betula alba* bark, *Impatiens balsamina* bark, *Costus spicatus* root, *Allium sativum* bulb and *Cyperus rotundus* root.

21 Claims, No Drawings

HERBAL COMPOSITION AND METHOD OF TREATING HIV INFECTION

RELATED APPLICATIONS

This application claims priority from U.S. Provisional Patent Application Ser. No. 60/471,928 which was filed on May 19, 2003, the content of which is incorporated by reference.

BACKGROUND OF THE INVENTION

1. Field of the Invention

The subject invention relates to a therapeutic herbal composition which is potentially beneficial for immune enhancement, prophylaxis and treatment of cancer, AIDS, Epstein Barr syndrome, depression and the like, and as a blood tonic.

2. Description of the Related Art

Acquired immune deficiency syndrome, commonly known as AIDS, is a disease caused by a retrovirus called human immunodeficiency virus (HIV). First recognized in 1981, this devastating disease has spread out on an international scale with millions of people world-wide considered to be HIV-infected. The virus preferentially targets the helper T cells, which play a central role in the functioning of the immune system. In most cases the virus, once incorporated into the helper T cell, remains dormant for an unspecified period of time. Once activated, however, the virus rapidly destroys the helper T cells, thereby crippling the immune system. It is at this stage that the symptoms of AIDS become evident. These include:
- enlarged lymphoid glands;
- unexplained rapid weight loss and diarrhea;
- fever and night sweats;
- dermatitis and skin eruptions and lesions;
- diminished sensitivity to skin tests;
- memory disorder and behavioral changes;
- increased incidence of certain cancers. A common tumor of AIDS patients is Kaposi's sarcoma, resulting in purplish marks on the skin; and
- increased susceptibility to opportunistic infections that rarely infect normal individuals. It is these infections that generally cause the patient's death within a few years of the onset of symptoms.

Currently, there is no cure for AIDS and attempts to produce a vaccine have been hindered by the fact that the virus is capable of changing its outer membrane configuration.

Although the use of various herbs has been described in related areas, the synergistic combination of the subject invention has never previously been described.

Turmeric extract prepared from *Curcuma longa* was shown in Japanese Patent Publication No. 4,095,032 to stimulate transdermal absorption and to increase the effect of pharmacologically active components. Likewise, Japanese Publication No. 4,091,029 describes the combination of *Curcoma longa* and *Cinnamonmum cassia* to obtain a similar effect.

Japanese Patent Publication No. 4,005,237 teaches the combination of *Cinnamomum sieboldii* and *Allium sativum* for superoxide scavenging in the treatment of inflammatory disorders. German Patent Publication No. 3,724,341 teaches the use of *Cinnamomum zeylanicum* as an anti-inflammatory agent which exerts a synergistic anti-inflammatory effect in combination with *Pumica granitum* cortex, *Cardamon zingiberaceie* fruit and *Piper longum* fruit.

Japanese Patent Publication No. 2,069,431 discloses the use of *Curcuma longa* for use as an antioxidant in foods and pharmaceutical products.

German Patent Publication No. 1,767,469 teaches the use of *Allium sativum* for use in preparations having an anti-cancer, anti-bacterial and chemotherapeutic effect.

PCT Application PCT/US94/02183, published as WO 94/18993, is directed to a therapeutic herbal composition formed from the disclosed herbs. This reference does not disclose the unexpected activity related to the digestibility of the compounds as well as the storage stability which characterizes compositions to which effective concentrations of sodium chloride, more preferably, sea salt, have been added.

In view of the above, there exists a great need for therapeutic compositions useful in enhancing the immune system.

SUMMARY OF THE INVENTION

The composition of herbs described herein functions to augment the immune system through the synergistic interaction of the herbal components. The subject invention provides a therapeutic composition comprising *Boswelia carterii* stem resin, *Styrax benzoin* stem resin, *Cinnamomum zeylanicum* bark, *Curcuma zedoaria* root, *Syzygium aromaticum* fruit, *Nardostachys chinensis* root, *Betula alba* bark, *Impatiens balsamina* bark, *Costus spicatus* root, *Allilum sativum* bulb and *Cyperus rotundus* root in amounts effective to produce a physiological benefit in combination with an amount of sodium chloride, more preferably sea salt, which is effective to promote the digestibility (palatability) and storage stability of the therapeutic composition.

The various features of novelty which characterize the invention are pointed out with particularity in the claims annexed to and forming a part of the disclosure. For a better understanding of the invention, its operating advantages, and specific objects attained by its use, reference should be had to the following detailed description of the preferred embodiments of the invention.

DETAILED DESCRIPTION OF THE PRESENTLY PREFERRED EMBODIMENTS

The term "patient" or "subject" is used throughout the specification to describe a human to whom treatment with the compositions and methods according to the present invention is provided.

The term "effective concentration" or "effective amount" is used to describe an amount or concentration of an active agent or composition according to the present invention which is used in the present invention to produce an intended result. In the case of the present invention, effective concentrations are generally concentrations which are effective to treat AIDS, Epstein Barr virus, cancer, depression and for use as a general blood tonic, which may include concentrations of the active agent which prevent these conditions as well. The term effective concentration or amount subsumes the administration of a pharmaceutically active agent according to the present invention for a period consistent with the realization of the intended result. Effective amounts of the compounds which are used according to the present invention include amounts which comprise approximately 250 mg to about 750 mg., more preferably about 600 mg. taken 1 to 8 times per day. These amounts of herbal product produce an effective concentration range in human body fluids, i.e., blood, plasma and serum.

The term "sea salt" is used to describe preferred salt which is used in the present invention to promote the digestibility and storage stability of compositions according to the present invention. Although any source of sodium chloride may be used in the present invention, provided that the amount of sodium chloride represents approximately 1% to about 20% by weight, more preferably about 3% to about 5% by weight of the final composition, salt obtained by the evaporation of salt water obtained from the ocean or sea, and in particular the Dead Sea, is preferred. Numerous sources of salt are proposed for use in the present invention.

The subject invention will now be described in terms of its preferred embodiments. These embodiments are set forth to aid in the understanding of the subject composition and method of use. However, these preferred embodiments are not to be construed as limiting. The subject composition comprises eleven plants of the following list for typical administration:

TABLE 1

| Ingredients | wt. | % by wt. | Range (wt. %) |
|---|---|---|---|
| *Boswelia carterii* stem resin | 90 mg | 15.5 | 1.5–75 |
| *Styrax benzoin* stem resin | 90 mg | 15.5 | 1.5–75 |
| *Cinnamomum zeylanicum* bark | 40 mg | 6.9 | 0.7–35 |
| *Curcuma zedoaria* root | 35 mg | 6.0 | 0.6–30 |
| *Syzygium aromaticum* fruit | 35 mg | 6.0 | 0.6–30 |
| *Nardostachys chinensis* root | 35 mg | 6.0 | 0.6–30 |
| *Betula alba* bark | 90 mg | 15.5 | 1.5–75 |
| *Impatiens balsamina* bark | 90 mg | 15.5 | 1.5–35 |
| *Costus spicatus* root | 25 mg | 4.3 | 0.4–25 |
| *Allilum sativum* bulb | 25 mg | 4.3 | 0.4–25 |
| *Cyperus rotundus* root | 25 mg | 4.3 | 0.4–25 |
| Total | 580 mg | 100 | 100 |

The above compositions are preferably combined with between about 1% and 20% by weight (final weight of the composition which includes the herbal combination plus sodium chloride) of sodium chloride, preferably in the form of sea salt, most preferably dead sea salt. Preferably, the amount of sodium chloride included ranges from about 3% to about 5% by weight, most preferably about 3% by weight.

The above herbs are typically dried and ground to a fine powder. All weights are expressed in milligrams and all percentages are by weight of the essential elements in the composition. The composition is typically an intimate mixture of powders. However, extracted herbs may also be used. The composition is then combined with effective amounts of sodium chloride, more preferably sea salt, in amounts effective to substantially enhance the digestibility and the storage stability of the composition. This amount generally ranges from about 1% to about 20% by weight of the composition, more preferably about 3% to about 5% by weight of the composition. 3% by weight of salt is most preferably included in the present compositions.

The known biological active components include choline and thiamine. Under normal conditions a 580 mg dose would be administered several times daily. The dosage, of course, may vary depending on body weight and other conditions readily determinable by those skilled in the art who have read the subject application. Administration is typically oral, with administration being via, e.g., a capsule, tablet, or cachet. For example, the composition can be made in a caplet form. In addition to the above herbs, various pharmaceutically acceptable additives, excipients and/or fillers, such as ash, may be present.

A unique natural composition derived from plant extracts has been demonstrated to overcome many of the debilitating symptoms of AIDS. This composition, which is typically orally ingested, represents a breakthrough in the pharmaceutical management of AIDS patients. Pilot studies have demonstrated that the subject composition causes:

reversal of gland swelling;
restoration of feeling of well being and associated weight gain;
improvement in response to skin hypersensitivity tests; and
increase in the circulating concentration of helper T cells (CD4-positive cells). Associated with this is an improvement in the CD4/CD8 ratio, with many patients returning to a normal ratio.

It is expected that the optimal time for therapy with the subject composition should commence in relation to the first appearance of symptoms, or may be used as a prophylactic prior to any indications.

Pilot studies on the effectiveness of the subject composition in protecting AIDS patients against depletion of the helper T cells have been conducted in several countries.

EXAMPLE 1

In Australia, fifteen patients have been evaluated to determine the clinical responses in AIDS-affected patients to the administration of the subject composition.

Four capsules of the subject composition as listed in Table 1 (containing 3% by weight of seal salt obtained from the Dead Sea were taken orally twice daily (morning and evening), one hour before meals. The composition was shown to be a low toxicity product capable of dramatically elevating the population of helper T cells. Detailed hematological and biochemical tests were conducted on each patient. The following Table 2 shows the most significant clinical data obtained from pilot studies on the effectiveness of the subject composition in protecting AIDS-infected patients from the debilitating effects of the disease.

TABLE 2

| Patient | Duration of treatment (months) | CD4/CD8 ratio Before | CD4/CD8 ratio After | Fold increase | Body weight (kg) Before | Body weight (kg) After | Body weight (kg) Gain |
|---|---|---|---|---|---|---|---|
| A.L. | 23.3 | 0.71 | 0.86 | 1.2 | 74.0 | 78.4 | 4.4 |
| L.W. | 19.8 | 0.66 | 1.68 | 2.5 | 69.0 | 81.0 | 12.0 |
| P.Y. | 18.0 | 0.60 | 1.39 | 2.3 | 49.0 | 54.0 | 5.0 |
| H.C. | 17.2 | 0.55 | 1.40 | 2.5 | 57.4 | 72.6 | 15.2 |
| D.F. | 11.8 | 0.15 | 0.16 | 1.1 | 51.0 | 64.0 | 13.0 |
| P.P. | 7.6 | 0.12 | 0.35 | 2.9 | 78.2 | 74.3 | −3.9 |
| D.A. | 5.2 | 0.50 | 0.95 | 1.9 | 58.9 | 69.4 | 10.5 |
| M.J. | 5.0 | 0.24 | 1.10 | 4.6 | N/A | N/A | N/A |
| B.S. | 4.9 | 0.18 | 0.41 | 2.3 | 71.4 | 74.0 | 2.6 |
| D.C. | 4.9 | 0.15 | 0.21 | 1.4 | 63.0 | 68.0 | 5.0 |
| J.M. | 4.7 | 0.25 | 1.30 | 5.2 | 67.0 | 80.0 | 13.0 |
| J.A. | 4.3 | 0.70 | 0.88 | 1.3 | 51.9 | 54.6 | 2.7 |
| N.O. | 4.2 | 1.19 | 1.25 | 1.1 | 63.5 | 70.9 | 7.4 |
| G.S. | 2.5 | 0.10 | 0.25 | 2.5 | N/A | N/A | N/A |
| P.C. | 2.0 | 0.27 | 0.37 | 1.4 | N/A | N/A | N/A |
| MEAN | | 0.42 | 0.84 | 2.0 | 62.9 | 70.1 | 7.2 |

Of the fifteen patients, the mean CD4/CD8 ratio (ratio of helper T cells to cytotoxic T cell and suppressor T cells) at the commencement of treatment was 0.42 ±0.08. (Note: The ratio in a healthy population is 1.0–3.5.) After a treatment period ranging from 2–23 months the CD4/CD8 ratio had significantly increased by two-fold to 0.84±0.14 ($p<0.001$).

Concurrently with this change was an improvement in the response to skin hypersensitivity tests and a general increase in well-being. This latter effect is demonstrated by the overall restoration of body weight, increasing from 62.9 to 70.1 kg, a weight gain of 7.2 kg (p<0.001).

Of the ten patients commencing treatment with a CD4/CD8 ratio greater than 0.20, 60% had ratios in the range of normal, healthy people by the last date of assessment. For the five patients commencing with a CD4/CD8 ratio less than 0.20, non had ratios in the normal range, although the ratio had increased twofold in value Before: 0.14±0.02; After: 0.28±0.05).

EXAMPLE 2

In India, six patients have been evaluated to determine the clinical responses in AIDS-affected patients to the administration of the subject composition.

The six patients were selected based on never having been prescribed any HIV/AIDS drug. ELISA and Western Blot test confirmed this absence of HIV/AIDS.

The patients took caplets of the herbal mixture as listed in Table 1 in combination with 3% seal salt obtained from the Dead Sea by weight based on the total weight of the herbal mixture and the sea salt. Each caplet comprises 1000 mg of the herb mixture.

The study lasted for one month. Before the beginning of the study, hemoglobin, weight and CD4 levels were measured. After this, patients began to take two caplets in the morning and two caplets in the evening. At the end of the study, hemoglobin, weight, and CD4 levels were measured again. The results are shown in Table 3.

TABLE 3

| | | | HGB | | Weight Kg | | CD4 | |
|---|---|---|---|---|---|---|---|---|
| Patient | Sex | Age | Before | After | Before | After | Before | After |
| 1 | M | 36 | 13.2 | 14 | 59.1 | 62 | 182 | 172 |
| 2 | F | 42 | 14.8 | 15.6 | 40.8 | 42.2 | 150 | 162 |
| 3 | F | 21 | 13.6 | 13.4 | 42.9 | 51.5 | 346 | 437 |
| 4 | F | 32 | 11.6 | 10.5 | 37.7 | 37.7 | 180 | 214 |
| 5 | F | 24 | 13.3 | 13 | 49.3 | 49.3 | 236 | 263 |
| 6 | F | 25 | 14.4 | 13.7 | 39.5 | 40 | 343 | 440 |

As shown in Table 3, the study results show that:
1. In five out of the six patients—CD4 levels increased.
2. In five out of six subjects—CD4 levels increased by ten percent or more.

The chief function of the immune system is to protect against infection, by destroying and eliminating invading organisms and any toxic molecules they produce. The immune response is a highly sophisticated defense system, without an organism would die as a result of bacterial, viral, fungal, or parasitic infection. This protection against entry of foreign organisms into the tissues is, to a large extent, dependent on a particular type of white blood cell called the lymphocyte. Lymphocytes are found in large numbers in the blood and the lymph (the colorless fluid in the lymphatic vessels that connect the lymph nodes of the body) and in specialized lymphoid organs, such as the thymus, lymph nodes, spleen, tonsils and appendix.

Lymphocytes can be separated into two major classes based on the type of immune response. Both classes, called B cells and T cells, arise from common stem cells in the bone marrow. When produced in the bone marrow, lymphocytes are immature and require further processing in order to become mature, functional cells. In mammals some cells differentiate within the bone marrow to become B cells, whereas others are processed in the thymus to generate T cells. These two cell types also differ in terms of their response to foreign substances, called antigens. Binding of an antigen transforms a B cell into a plasma cell, which is responsible for humoral or antibody-mediated immunity. The plasma cell produces and secretes antibodies which bind to an invading cell, either causing it to be inactivated or targeting it for removal from the body.

A second type of response, involving T cells, is called cell-mediated immunity. This involves the production of specialized cells that react with foreign antigens on the surface of other host cells. The effector cell can kill a virus-infected host cell that has viral proteins on its surface, thereby eliminating the infected cell before the virus has replicated. In other situations the reacting cell activates macrophages to destroy the foreign microorganism. The cell-mediated immune response is also responsible for the rejection of skin grafts and organ transplants.

Although the main function of the immune system is to save us from disease-causing microorganisms, the system cannot actually distinguish between pathogenic and non-pathogenic organisms. Rather, it is because they are recognized as foreign (or non-self) that our immune system is induced to react against them. Before B cells differentiate to mature antibody-secreting cells, called plasma cells, they carry their antibodies as membrane-bound surface molecules. These antibodies act as cell surface receptors for antigens, thereby providing a means of distinguishing foreign invading cells from the body's own cells. When an antigen (associated with a bacteria, virus, etc.) interacts with a corresponding cell-surface receptor on an immature B cell, the specific binding, together with other cellular interactions, triggers the proliferation and maturation of that particular B cell. The resultant plasma cells secrete antibodies of the same specificity as the original antibody on the surface of the immature B cell.

The process whereby antigens stimulate division and maturation of B cells to which they bind is referred to as clonal selection. This term is derived from the proposal that the immune system contains many millions of different families, or clones, of B cells each committed to make one particular antibody. The presence of a foreign antigen is immediately recognized by one (or more) of these millions of clones, and those that react with the antigen are induced to proliferate and mature. Each cell produced from a clone therefore produces the same antibody and this leads to a build-up of the specific antibody. These antibody molecules are then directed against the foreign antigen. If the foreign antigen is toxic, binding of antibody generally inactivates the toxin. If it is an invading microorganism, antibody binding leads to destruction of the microorganism.

It is now recognized that although the B cells are responsible for the production of antibodies, a complex cellular interaction is required in order to activate this process. Central in this process are a specific type of T lymphocytes, the helper T cells ($T_H$ cells), which enhance the activation of the B cells. Although the details of this activation event are still being determined, it is known that the presence of a foreign organism (antigen) within our body causes macrophages to bind the antigen and process it. The processed antigen is then presented to the B cells and helper T cells. The helper T cells respond by releasing growth factors, called interleukins (or lymphokines), which stimulate cell division and maturation of the B cells, ultimately inducing the production of memory cells and plasma cells, which are specialized for producing large quantities of antibodies.

T lymphocytes are involved in two very different types of cellular immune responses. One is to destroy cells that contain foreign antigens on their surface, as occurs when a host cell becomes infected with a virus. Thus, often the target cells are an individual's own cells shortly after they have become infected by a virus. The cells responsible for this response are referred to as cytotoxic T cells. Because viruses proliferate within cells, where they are protected from attack by antibodies, the cytotoxic T cells provide an important defense against the spreading of the viral infection to other cells, by destroying the infected cell before virus proliferation and assembly has occurred. Cytotoxic T cells are also responsible for the rejection of skin grafts and organ transplants.

When an antigen binds to the immature T cell via specific cell-surface receptors, the cell is transformed into a lymphoblast which divides to produce a population of activated T cells. These T cells subsequently differentiate to produce cytotoxic T cells, memory cells, helper T cells ($T_H$ cells) and suppressor T cells ($T_S$ cells). The latter two cell types represent the majority of the T lymphocyte cell population and are responsible for the second major function of the T lymphocytes, that is the regulation of the immune system.

The $T_H$ cells are critical in facilitating the response of both B cells (as discussed earlier) and the cytotoxic T cells. As a consequence, any reduction in the circulating level Of $T_H$ cells leads to a dramatically impaired immune response.

The $T_S$ cells have the opposite effect by blocking B and T cell responses. Thus, although cytotoxic T cells and B cells are the cells directly responsible for the immune responses against infection, their effectiveness in the elimination of the infection is dramatically modulated by the relative level of helper T cells and suppressor T cells in the blood.

The various classes of T lymphocytes are small, round cells which are not readily distinguishable under the microscope. They can be identified, however, by the presence of specific glycoproteins that are present on their surface (see Table 2). Whereas all T cells have the CD3 glycoprotein, only helper T cells have the CD4 glycoprotein and both cytotoxic T cells and suppressor T cells have the CD8 glycoprotein. The importance of these differences is that they can be used to determine the relative concentration of the various types of T cells. For instance, the CD4/CD8 ratio can be used to determine the concentration of helper T cells relative to the concentration of both the cytotoxic and suppressor T cells. Table 4 shows the presence or absence of specific glycoproteins on the surfaces of various types of T lymphocytes.

TABLE 4

| Cell type | Cell surface Glycoprotein* | | |
|---|---|---|---|
| | CD3 | CD4 | CD8 |
| Helper T cells (TH) | + | + | − |
| Cytotoxic T cells | + | − | + |
| Suppressor T cells ($T_S$) | + | − | + |

*+ means that glycoprotein is present;
− means that glycoprotein is absent.

The host cell for the human immunodeficiency virus (HIV) is the helper T cell ($T_H$ cell). Indeed, the disease is transmitted when a $T_H$ cell, infected by the virus, is transferred through the blood or via semen or vaginal secretion, to an uninfected individual. The $T_H$ cells of that individual immediately recognize the virus-infected cell as foreign. However, before any immune response can be invoked, the foreign HIV particles have bound to the $T_H$ cells, been incorporated into the cells and rendered them inactive. The virus is surrounded by a lipid bilayer membrane containing two glycoproteins, one of which binds tightly to the CD4 protein on the membrane of the $T_H$ cells. Thus, one of the features which distinguish them from other T cells, namely the presence of the CD4 protein on their surface, renders them susceptible to attack. Once bound, the membranes of the cell and virus fuse and the genetic elements of the virus are readily incorporated into the genetic material of the host cell.

As the virus is transferred from one $T_H$ cell to another in the infected individual, an increasing proportion of the immune system is disabled, since the cells that are essential for mounting an immune response are rapidly being destroyed. The HIV virus may lie dormant inside the infected $T_H$ cells for some time. However, once stimulated, the proliferation of the virus-infected cells overwhelms the remaining uninfected $T_H$ cells and the immune system is rapidly rendered ineffective. The depletion of the $T_H$ cell population can be clinically evaluated by measuring the CD4/CD8 ratio, which is a measure of the $T_H$ cell population relative to that of the cytotoxic T cells and the $T_S$ cells.

In summary, infection by the AIDS virus leads ultimately to the destruction of the $T_H$ cell population. Because of the key regulatory role of this particular cell population, which is essential for both the adequate functioning of the B cells (antibody response) and the cytotoxic T cells (cell-mediated response), the entire immune system is rendered quite inactive. The infected individual is then prone to a greater incidence of certain cancers and to infection by other opportunistic microorganisms. It is this latter effect that frequently leads to the death of the infected person. The subject composition, by being able to elevate the $T_H$ cell population, has the potential to prolong the life of AIDS sufferers by restoring the T cell profile to normal levels.

Testing results of capsules containing the subject composition show that the product complies with the British Pharmacopoeia specifications during its two year shelf life. The herbal powder is packed into moisture permeable gelatine capsules of zero size and next in 350 ml polyvinyl chloride bottles stored at range temperature 20–30° C. Susceptibility to moisture absorption change during storage and distribution was from 5.6% to 12% (an acceptable level). The batch studies of pH aqueous solutions indicate an inherent characteristic value between 4.4 and 4.8.

In degradation pathways of the digestibility test within pepsin solution according to Association of Official Analytical Chemists, 28% of the subject powder is digested during 16 hours at a temperature of 42–45° C. A method is applicable within 0.2% pepsin concentration demonstrating good market quality. Further comparative studies of digestibility for extracted powder of diethyl ether, chloroform and ethyl alcohol conform a stable minimum for protein decomposition for standard batches otherwise increasing a degradation in bioactive reactions. Moreover, data accumulated from clinical trials on the effectiveness of the subject composition in protecting AIDS-infected patients from the debilitating effects of the disease illustrate 2.5 fold increase with CD4/CD8 ratio during time ranging from 2.5–24 months. (Ratio of helper T cells to cytotoxic T cell and suppressor T cells). Secondly, the mean hemoglobin concentration was 11.19 g/dL at the commencement of treatment, but was significantly elevated (p<0.001) to 14.3 g/dL after a treatment period (a 20.4% increase).

The subject powder maintains a brown color and does not lose its character under the cycling effect of night and day. Smell and taste are unchanged during storage.

Alternative solubility of the subject composition in organic solvents, e.g. dichloromethane, chloroform and ethyl alcohol at room temperature and at 40°, 60° and 70° C., identify the product with a dissolution rate of 26–56%. However, the batches are sterilized within radiation or by ethylene oxide, the stability records show a lack of detectable amounts of degradation products and systematic bacteriological tests under conditions of high humidity proved satisfactory.

Upon reading the subject application, various alternative embodiments will become obvious to those skilled in the art. These embodiments are to be considered within the scope and spirit of the subject invention, which is only to be limited by the claims which follow and their equivalents.

I claim:

1. A therapeutic composition comprising a herbal mixture formed by *Boswelia carterii* stem resin, *Styrax benzoin* stem resin, *Cinnamomum zeylanicum* bark, *Curcuma zedoaria* root, *Syzygium aromaticum* fruit, *Nardostachys chinensis* root, *Betula alba* bark, *Impatiens balsamina* bark, *Costus spicaius* root, *Allium sativum* bulb and *Cyperus rotundus* root in amounts effective to produce a physiological benefit in combination with an amount of sodium chloride effective to promote the digestibility and storage stability of the composition.

2. The composition of claim 1 wherein the sodium chloride is in an amount ranging from about 1% to about 20% by weight based on the total weight of the herbal mixture and the sodium chloride.

3. The composition according to claim 1, wherein by weight based on the total weight of the herbal mixture, the herbal mixture comprises from about 1.5% to about 75% *Boswelia carterii* stem resin; from about 1.5% to about 75% *Styrax benzoin* stem resin; from about 0.7% to about 35% *Cinnamomum zeylanicum* bark; from about 0.6% to about 30% *Curcuma zedoaria* root; from about 0.6% to about 30% *Syzygium aromaticum* fruit; from about 0.6% to about 30% *Nardostachys chinensis* root; from about 1.5% to about 75% *Betula alba* bark; from about 1.5% to about 35% *Impatiens balsamina* bark; from about 0.4% to about 25% *Costus spicatus* root; from about 0.4% to about 25% *Allium sativum* bulb; and from about 0.4% to about 25% *Cyperus rotundus* root.

4. The composition of claim 1 wherein the sodium chloride is in an amount ranging from about 3% to about 5% by weight based on the total weight of the herbal mixture and the sodium chloride.

5. The composition of claim 1 wherein by weight based on the total weight of the herbal mixture, the herbal mixture comprises about 15.5% *Boswelia carterii* stem resin; about 15.5% *Styrax benzoin* stem resin; about 6.9% *Cinnamomum zeylanicum* bark; about 6.0% *Curcuma zedoaria* root; about 6.0% *Syzygium aromaticum* fruit; about 6.0% *Nardostachys chinensis* root; about 15.5% *Betula alba* bark; about 15.5% *Impatiens balsamina* bark; about 4.3% *Costus spicatus* root; about 4.3% *Allium sativum* bulb; and about 4.3% *Cyperus rotundus* root.

6. The composition of claim 1 wherein the composition comprises about 3% sodium chloride by weight based on the total weight of the sodium chloride and the herbal composition.

7. The composition of claim 1 wherein the sodium chloride is in the form of sea salt.

8. The composition of claim 7 wherein the sea salt is obtained from Dead Sea.

9. The composition of claim 1 further comprising at least one of a pharmaceutically acceptable additive, excipient, and filler.

10. The composition of claim 1 wherein the composition is in an oral dosage form selected from the group consisting of capsule, tablet, and sachet.

11. The composition of claim 10 wherein each unit dosage of the composition comprises about 90 mg *Boswelia carterii* stem resin; about 90 mg *Styrax benzoin* stem resin, about 40 mg *Cinnamomum zeylanicum* bark; about 35 mg *Curcuma zedoaria* root; about 35 mg *Syzygium aromaticum* fruit; about 35 mg *Nardostachys chinensis*; about 90 mg *Betula alba* bark; about 90 mg *Impatiens balsamina* bark; about 25 mg *Costus spicatus* root; about 25 mg *Allium sativum* bulb; about 25 mg *Cyperus rotundus* root; and sodium chloride in an amount ranging from about 1% to about 10% by weight based on the total weight of the herbal mixture and sodium chloride.

12. The composition of claim 10 wherein each unit dosage of the composition comprises about 1000 mg of the herb mixture.

13. The composition of claim 1 wherein the composition is in the form of oral caplet.

14. A method of treating AIDS comprising administering a patient a composition which comprises a herbal mixture formed by *Boswelia carterii* stem resin, *Styrax benzoin* stem resin, *Cinnamomuin zeylanicum* bark, *Curcuma zedoaria* root, *Syzygium aromaticum* fruit, *Nardostachys chinensis* root, *Betula alba* bark, *Impatiens balsamina* bark, *Costus spicatus* root, *Allium sativum* bulb and *Cyperus rotundus* root in amounts effective to produce a physiological benefit in combination with an amount of sodium chloride effective to promote the digestibility and storage stability of the composition.

15. The method of claim 14 wherein the sodium chloride is in an amount ranging from about 1% to about 20% by weight based on the total weight of the herbal mixture and the sodium chloride.

16. The method of claim 14 wherein by weight based on the total weight of the herbal mixture, the herbal mixture comprises from about 1.5% to about 75% *Boswelia carterii* stem resin; from about 1.5% to about 75% *Styrax benzoin* stem resin; from about 0.7% to about 35% *Cinnamomum zeylanicum* bark; from about 0.6% to about 30% *Curcuma zedoaria* root; from about 0.6% to about 30% *Syzygium aromaticum* fruit; from about 0.6% to about 30% *Nardostachys chinensis* root; from about 1.5% to about 75% *Betula alba* bark; from about 1.5% to about 35% *Impatiens balsamina* bark; from about 0.4% to about 25% *Costus spicatus* root; from about 0.4% to about 25% *Allium sativum* bulb; and from about 0.4% to about 25% *Cyperus rotundus* root.

17. The method of claim 14 wherein the composition is in an oral dosage form selected from the group consisting of capsule, tablet, and cachet.

18. The method of claim 17 wherein each unit dosage of the composition comprises about 90 mg *Boswelia carterii* stem resin; about 90 mg *Styrax benzoin* stem resin, about 40 mg *Cinnamomum zeylanicum* bark; about 35 mg *Curcuma zedoaria* root; about 35 mg *Syzygium aromaticum* fruit; about 35 mg *Nardostachys chinensis*; about 90 mg *Betula alba* bark; about 90 mg *Impatiens balsamina* bark; about 25 mg *Costus spicatus* root; about 25 mg *Allium sativum* bulb; about 25 mg *Cyperus rotundus* root; and sodium chloride in an amount ranging from about 1% to about 10% by weight based on the total weight of the herbal mixture and sodium chloride.

19. The method of claim 18 wherein the patient is administered several times daily.

20. The method of claim 18 wherein the patient is daily administered four units dosage in the morning, and four units dosage in the evening, about one hour before meals.

21. The method of claim 14 wherein the composition is in caplet form.

* * * * *